United States Patent
Steube et al.

(10) Patent No.: US 9,125,600 B2
(45) Date of Patent: Sep. 8, 2015

(54) MEDICAL DEVICE WITH INCORPORATED DISINFECTING WIPE AND METHOD OF USING SAME

(76) Inventors: Gregory A. Steube, St. Charles, MO (US); Richard L. Fiser, Wildwood, MO (US); Michael J. Noble, St. Charles, MO (US); Janice L. Sherman, Chesterfield, MO (US)

( * ) Notice: Subject to any disclaimer, the term of this patent is extended or adjusted under 35 U.S.C. 154(b) by 1317 days.

(21) Appl. No.: 12/819,288

(22) Filed: Jun. 21, 2010

(65) Prior Publication Data

US 2010/0331726 A1 Dec. 30, 2010

Related U.S. Application Data

(60) Provisional application No. 61/221,220, filed on Jun. 29, 2009.

(51) Int. Cl.
| | |
|---|---|
| *A61B 17/32* | (2006.01) |
| *A61B 17/14* | (2006.01) |
| *A61B 5/15* | (2006.01) |
| *A61B 5/153* | (2006.01) |
| *A61M 5/00* | (2006.01) |
| *A61M 5/31* | (2006.01) |

(52) U.S. Cl.
CPC .............. *A61B 5/1411* (2013.01); *A61B 5/153* (2013.01); *A61M 5/002* (2013.01); *A61M 5/3129* (2013.01)

(58) Field of Classification Search
CPC ... A61M 5/3135; A61M 5/02; A61M 5/3129; A61F 13/38; A61F 13/40; A61B 5/154; A61B 5/153

USPC .......................................................... 600/576
See application file for complete search history.

(56) References Cited

U.S. PATENT DOCUMENTS

| | | | |
|---|---|---|---|
| 2,652,149 A | | 9/1953 | O'Meara |
| 2,851,036 A | * | 9/1958 | Lipari ............................ 600/578 |
| 3,280,420 A | * | 10/1966 | Wanzenberg ..................... 401/7 |
| 3,341,003 A | | 9/1967 | Marsh |
| 3,346,104 A | | 10/1967 | Marsh |
| 3,515,265 A | | 6/1970 | Bartnik |
| 3,680,559 A | | 8/1972 | Gorbahn |
| 4,189,053 A | | 2/1980 | Stagnitto et al. |
| 4,243,035 A | | 1/1981 | Barrett |
| 4,344,532 A | | 8/1982 | Eldridge, Jr. et al. |
| 4,648,408 A | | 3/1987 | Hutcheson et al. |
| 4,799,926 A | | 1/1989 | Haber |
| 4,811,845 A | | 3/1989 | Baggett |
| 5,109,984 A | | 5/1992 | Romick |
| 5,291,990 A | | 3/1994 | Sejzer |
| 5,470,323 A | * | 11/1995 | Smith et al. ................... 604/289 |
| 5,803,499 A | | 9/1998 | Tung et al. |

(Continued)

OTHER PUBLICATIONS

European Search Report regarding related application serial No. EP 10167648.4 dated Aug. 25, 2011—6 pgs.

*Primary Examiner* — Brian Szmal
*Assistant Examiner* — H. Q. Nguyen
(74) *Attorney, Agent, or Firm* — Lisa E. Winsor, Esq.

(57) ABSTRACT

A medical device including a barrel having an open first end and capable of supporting a needle at a second end of the barrel is provided and includes a lid releasably adhered to and overlying the open first end of the barrel in a fluid tight manner; and a pad secured to a surface of the lid such that the pad is disposed within a cavity of the barrel when the lid is adhered to the barrel, wherein the pad comprises a disinfecting solution.

25 Claims, 8 Drawing Sheets

(56) References Cited

U.S. PATENT DOCUMENTS

| | | |
|---|---|---|
| 5,894,923 A | 4/1999 | Hamstra et al. |
| 6,073,767 A | 6/2000 | Cohen et al. |
| 6,225,522 B1 | 5/2001 | Schroeder |
| 6,669,236 B1 | 12/2003 | Höllwarth-Oberholz |
| 6,715,609 B1 | 4/2004 | Gupton |
| 7,126,879 B2 | 10/2006 | Snyder |
| 2007/0131577 A1 | 6/2007 | Call |
| 2007/0167917 A1 | 7/2007 | Lee |
| 2008/0155941 A1 | 7/2008 | Williams-Hartman |

* cited by examiner

FIG. 14

MEDICAL DEVICE WITH INCORPORATED DISINFECTING WIPE AND METHOD OF USING SAME

RELATED APPLICATIONS

This application claims priority to U.S. provisional application Ser. No. 61/221,220, filed Jun. 29, 2009 and entitled BLOOD COLLECTION DEVICE WITH INCORPORATED DISINFECTING WIPE, which is incorporated herein by reference in its entirety for all purposes.

BACKGROUND

1. Technical Field

The present disclosure relates to medical devices and, more specifically, to medical needle devices, e.g., blood collection devices and syringes, incorporating a disinfecting wipe and methods for their use.

2. Background of Related Art

Typically, in practice today, prior to insertion of a hypodermic needle or the like into a patient, the area of the skin of the patient that is to be pierced by the hypodermic needle, is disinfected with a swab or a wipe that is impregnated with alcohol, benzalkonium chloride or the like. Such swabs or wipes are typically kept separate and apart from the medical device (e.g., a blood collection device) that is going to be used to pierce the skin of the patient. Many swabs, such as cotton balls, gauze pads, wipes and the like may be stored dry and thus require a degree of wetting in order to be used to properly prepare the skin of the patient, or are stored is a vapor-sealed package kept separate and apart from the medical device.

As such, the process of preparing the skin of a patient for the piercing by a hypodermic needle or the like is involved and requires numerous procedural steps to be taken by a nurse or phlebotomist in order to conform with proper medical procedure.

Thus, a need exists for a simpler, more efficient system and method of preparing a skin of a patient for piercing by the hypodermic needle or the like. For example, the need exists for a system that requires the gathering of fewer items prior to a skin puncture procedure.

A need exists for a medical needle device including a skin preparing swab or wipe supported therein or thereon.

SUMMARY

The present disclosure relates to medical devices and storage containers incorporating a disinfecting pad or the like and methods for their use.

According to an aspect of the present disclosure a medical needle device including a barrel having an open first end and capable of supporting a needle at a second end of the barrel is provided. The medical needle device includes a lid releasably connected to and overlying the open first end of the barrel; and a pad secured to the lid and disposed within a cavity of the barrel when the lid is connected to the barrel. The pad comprises a disinfecting solution.

The lid may be adhered to the barrel in a fluid tight and/or vapor tight manner. The lid may include a tab extending therefrom. The lid may be fabricated from a fluid impermeable material and/or a vapor impermeable material.

According to another aspect of the present disclosure, a medical needle device including a barrel having an open first end and capable of supporting a needle at a second end of the barrel is provided. The medical needle device comprises a lid releasably connected to the barrel. The lid includes a first layer releasably adhered to and overlying the open first end of the barrel; and a second layer releasably adhered to the first layer, wherein the first layer and the second layer define at least one of a fluid and vapor tight pocket therebetween. The medical needle device further comprises a pad disposed within the pocket of the lid, wherein the pad comprises a disinfecting solution.

The lid may include a tab extending from and integrally connected with the second layer. The second layer may be integrally connected to the first layer along a fold line. The lid may include an additional pad secured to the first layer at a location within the barrel. The pad may be secured to the first layer and/or the second layer within the pocket. The second layer may be integrally connected to the first layer along a fold line. The pad may be secured to and may extend between the first layer and the second layer.

The first layer and the second layer of the lid may be fabricated from a fluid impermeable material and/or a vapor impermeable material.

The first layer of the lid may include a flap extending therefrom and integrally connected therewith. The flap of the first layer may be releasably adhered to and may overlie the open first end of the barrel. The flap may be dimensioned such that the pocket of the lid is positionable against an outer surface of the medical needle device.

According to a further aspect of the present disclosure, a medical device including a barrel having an open first end and capable of supporting a needle at a second end of the barrel is provided. The medical device includes a lid releasably adhered to and overlying the open first end of the barrel in at least one of a fluid tight manner and a vapor tight manner; and a pad secured to a surface of the lid such that the pad is disposed within a cavity of the barrel when the lid is adhered to the barrel. The pad comprises a disinfecting solution.

The lid may include a tab extending therefrom. The lid may be fabricated from a fluid impermeable material and/or a vapor impermeable material.

According to still another aspect of the present disclosure, a method of collecting a fluid sample from a patient is provided and includes the step of providing a medical needle device including a barrel having an open first end and supporting a needle at a second end of the barrel. The medical needle device includes a lid releasably connected to and overlying the open first end of the barrel; and a pad secured to the lid and disposed within a cavity of the barrel when the lid is connected to the barrel, wherein the pad comprises a disinfecting solution. The method further includes the steps of peeling the lid away from the medical needle device to expose the pad; wiping the pad across an area of the skin of the patient to be penetrated by the needle of the medical needle device; and penetrating the skin of the patient, in the area wiped by the pad, with the needle of the medical needle device.

According to yet another aspect of the present disclosure, a method of collecting a fluid sample from a patient is provided and includes the step of providing a medical needle device including a barrel having an open first end and supporting a needle at a second end of the barrel. The medical needle device includes a lid releasably connected to the barrel. The lid includes a first layer releasably adhered to and overlying the open first end of the barrel; and a second layer releasably adhered to the first layer, wherein the first layer and the second layer define at least one of a fluid and vapor tight pocket therebetween. The medical needle device further includes a pad disposed within the pocket of the lid, wherein the pad comprises a disinfecting solution. The method further includes the steps of peeling the first layer of the lid at least partially away from the second layer of the lid to expose the pad; removing the pad from the pocket; wiping the pad across an area of the skin of the patient to be penetrated by the needle of the medical needle device; and penetrating the skin of the patient, in the area wiped by the pad, with the needle of the medical needle device.

According to a further aspect of the present disclosure, in combination, there is provided a medical storage container and a medical device. The medical device is configured to perform a surgical procedure on a patient; and the medical storage container has a body portion defining a cavity configured and dimensioned to receive the medical device. The container further includes a lid releasably secured to and overlying the body portion to enclose the cavity in at least one of a fluid tight and vapor tight manner, the lid defining at least one of a fluid tight and vapor tight pocket; and a pad disposed within at least one of a fluid tight and vapor tight pocket of the lid, wherein the pad comprises a disinfecting solution.

The disinfecting solution may be one of alcohol, isopropyl alcohol and benzalkonium chloride.

BRIEF DESCRIPTION OF THE DRAWINGS

Various embodiments of the presently disclosed medical needle device are disclosed herein with reference to the drawings, wherein.

DETAILED DESCRIPTION

Embodiments of the presently disclosed medical device and methods of use will now be described in detail with reference to the drawings wherein like reference numerals designate identical or corresponding elements in each of the several views.

In this description, the term proximal is generally used to indicate relative nearness of a referenced item to a user of the device and the term distal is used to indicate relative remoteness of a referenced item to a user of the device.

The present invention provides a medical device with incorporated disinfecting wipe and method of using same. As used herein, the term "medical device" is defined as any individually sealed or packaged single use or disposable medical device constructed and arranged to penetrate an area of skin of a patient. Examples of medical devices include, but are not limited to syringes and blood collection needles. As used, herein, the term "wipe" is synonymous with swabs, balls and pads. A disinfecting wipe may be formed of any material of construction capable of adsorbing or accumulating on its surface a disinfectant which may subsequently be transferred to a surface of a patient upon contact with the patient. A disinfecting wipe may be saturated with a disinfecting solution. Examples of materials of construction of the wipe include, but are not limited to swabs, such as cotton balls, gauze pads, and synthetic and natural fabrics.

Figure 1:
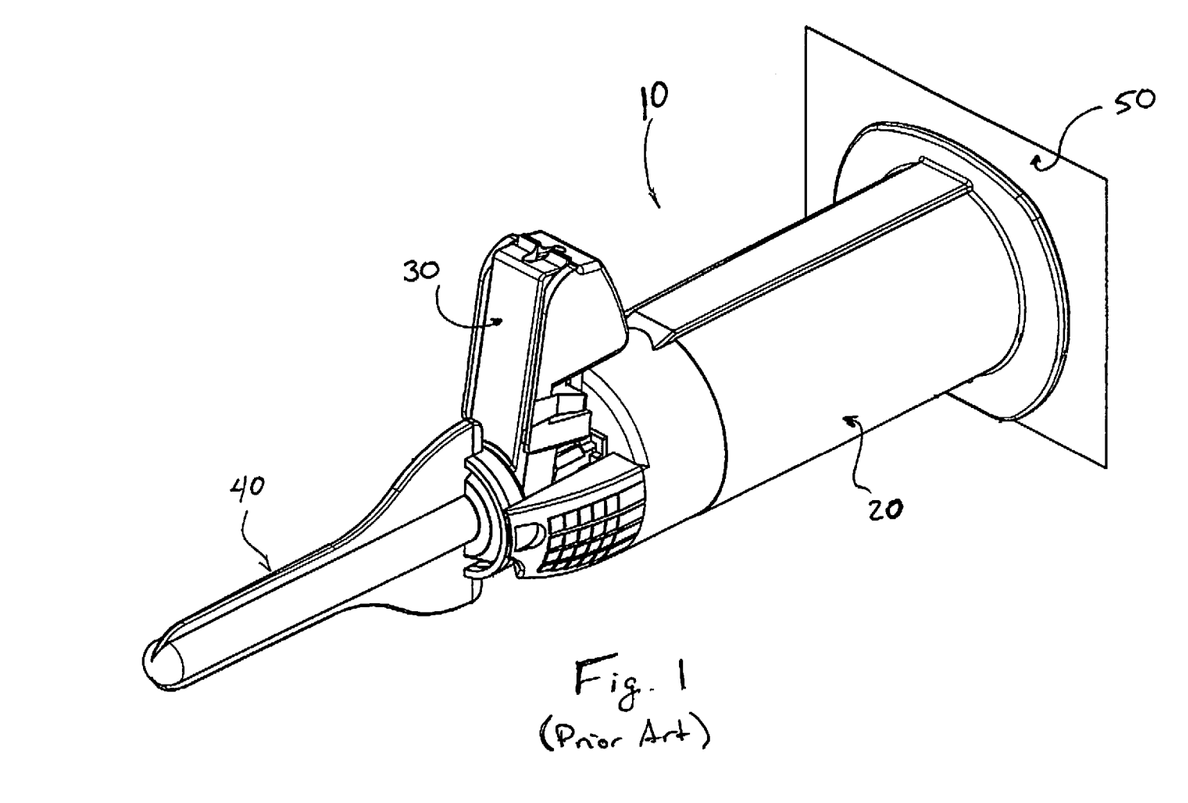
FIG. 1 is a perspective view of an exemplary prior art medical needle device.

As seen in FIG. 1, a prior art medical device, in the form of a blood collection device, is generally designated as 10. By way of illustration, blood collection device 10 includes a blood collector barrel 20 dimensioned to receive a blood collection vial or tube (not shown) therein. Blood collection device 10 may further include a safety shield apparatus similar to safety shield apparatus 30 mounted on a distal end of blood collector barrel 20, and a removable sheath 40 positioned about the distal end of the needle to cover the distal end of the needle until such time as blood collector device is to be used. As shown in FIG. 1, blood collection device 10 includes a peelable lid 50 secured to and extending across an open proximal end of blood collector barrel 20 using an adhesive or the like and can function to prevent dust or debris from entering blood collector barrel 20 or as a sterile barrier which assures sterility of blood collector barrel 20.

Figure 2:
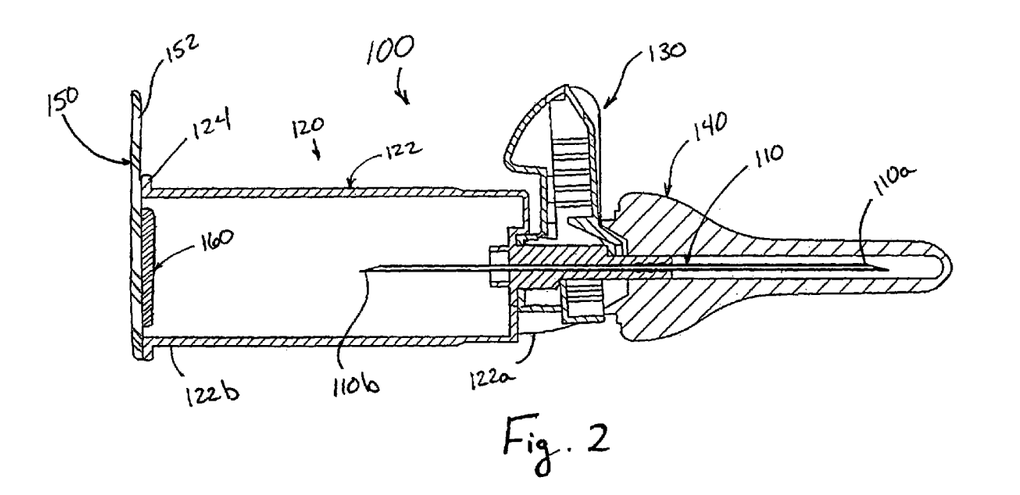
FIG. 2 is a longitudinal, cross-sectional view of a medical needle device according to an embodiment of the present disclosure.
Figure 3:
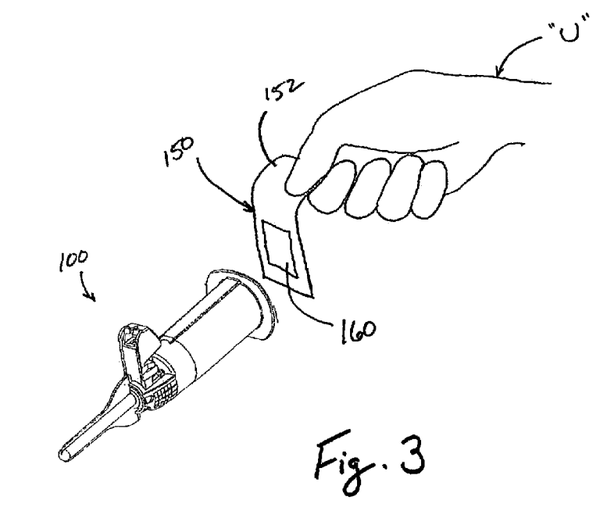
FIG. 3 is a schematic, perspective view of the medical needle device of FIG. 2, illustrating a method of use thereof.

Turning now to FIGS. 2 and 3, a medical needle device, in accordance with an embodiment of the present disclosure, is generally designated as 100. Medical needle device 100 includes a blood collector barrel 120 defining a cylindrical chamber 122 having a distal end 122a configured to support a needle 110 and an open proximal end 122b. Cylindrical chamber 122 is dimensioned to receive a blood collection vial (not shown) therein. Needle 110 may be a double-ended needle having a sharpened distal end 110a extending from distal end 122a of cylindrical chamber 122 and a sharpened proximal end 110b extending into blood collector barrel 120.

Medical needle device 100 further includes a safety shield apparatus 130 mounted on a distal end of blood collector barrel 120. Safety shield apparatus 130 includes an unactuated position wherein distal end 110a of needle 110 is unsheathed, and an actuated position wherein distal end 110a of needle 110 may be sheathed following a use of medical needle device 100. Medical needle device 100 also includes a removable sheath 140 positioned about distal end 110a of needle 110 to cover distal end 110a of needle 110 until such time as medical needle device 100 is to be used.

As shown in FIGS. 2 and 3, blood collector barrel 120 includes a finger flange 124 projecting radially outward from proximal end 122b of cylindrical chamber 122. Medical needle device 100 includes a peelable lid or the like 150 releasably secured to finger flange 124 using an adhesive or the like and can function to prevent dust or debris from entering cylindrical chamber 122, as a sterile barrier which assures sterility of cylindrical chamber 122, or create a fluid/vapor tight seal therewith.

With continued reference to FIGS. 2 and 3, peelable lid 150 is sized to overlie open proximal end 122b of cylindrical chamber 122, and includes a tab 152 extending therefrom for gripping by a user "U" in order to detach lid 150 from cylindrical chamber 122. Peelable lid 150 may include a metalized layer disposed on a paper or plastic film backing in order to reduce the incidence and degree of porosity thereof.

Lid 150 is provided with a pad, wipe, swab or the like 160 adhered, bonded or otherwise secured to a surface thereof. Pad 160 is secured to lid 150 such that pad 160 is disposed or retained within cylindrical chamber 122 when lid 150 is secured to finger flange 124 of blood collector barrel 120. Pad 160 comprises a disinfecting solution. In some embodiments, pad 160 is saturated with a quantity of a disinfecting solution or the like, such as, for example, alcohol, benzalkonium chloride, or a solution of 70% isopropyl alcohol. An exemplary 2-ply prep pad saturated with disinfecting solution is commercially available from Covidien AG (d/b/a Kendall, Mansfield, Mass.) and sold under the tradename Webcol® Alcohol Preps. By locating pad 160 within cylindrical chamber 122, the likelihood of pad 160 drying out is reduced.

In use, prior to the penetration of the skin of the patient with distal end 110a of needle 110, the skin of the patient is to be disinfected. In order to disinfect the skin of the patient, the user "U" separates or detaches lid 150 from cylindrical chamber 122 by peeling lid 150 away from cylindrical chamber 122 thus exposing pad 160. The user "U" then wipes or otherwise treats the skin of the patient, in the area which is to be penetrated (e.g., the needle insertion site), with pad 160 to disinfect said area. Following use of pad 160, lid 150 including pad 160 is discarded according to accepted medical practice.

Figure 4:
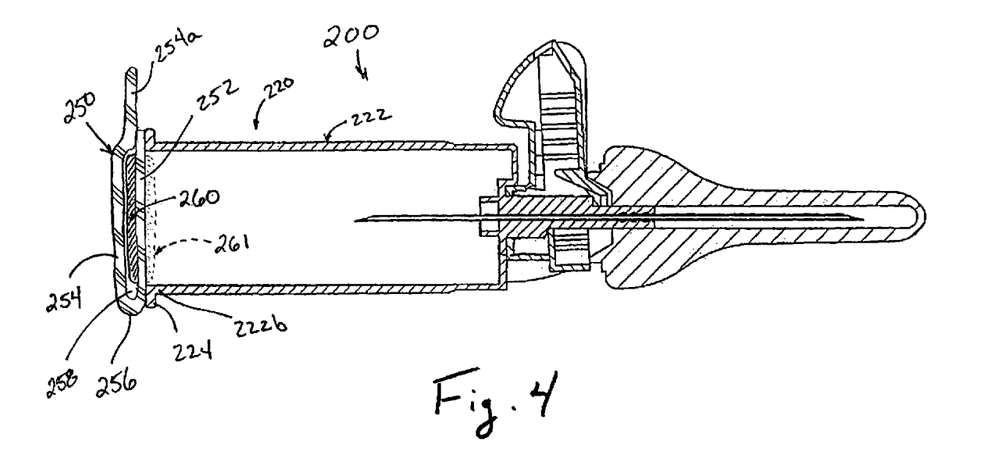
FIG. 4 is a longitudinal, cross-sectional view of a medical needle device according to another embodiment of the present disclosure.
Figure 5:
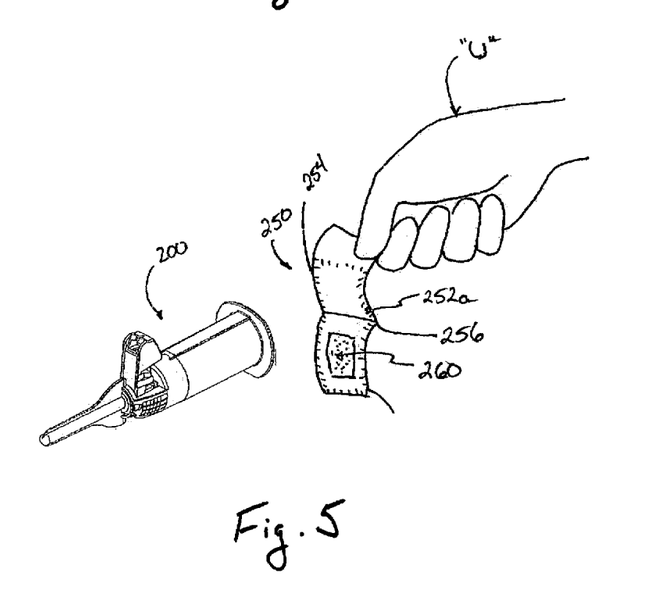
FIG. 5 is a schematic, perspective view of the medical needle device of FIG. 4, illustrating a method of use thereof.

Turning now to FIGS. 4 and 5, a medical needle device, in accordance with another embodiment of the present disclosure, is shown and generally designated as 200. Medical needle device 200 is substantially similar to medical needle device 100 and thus will only be discussed in detail to the extent necessary to identify differences in construction and operation thereof.

As shown in FIGS. 4 and 5, medical needle device 200 includes a peelable lid or the like 250 releasably secured to a finger flange 224 of blood collector barrel 220 in a fluid/vapor tight manner. Peelable lid 250 includes a first layer 252 sized to overlie open proximal end 222b of cylindrical chamber 222, and a second layer 254 connected to first layer 252 along a fold line 256. Second layer 254 is comparable in size to first layer 252 and defines a tab 254a extending therefrom for gripping by a user "U" in order to separate second layer 254 from first layer 252 and detach lid 250 from blood collector barrel 220, Second layer 254 overlies first layer 252 and may be releasably adhered to one another along a perimeter 252a of first layer 252 in order to define a fluid/vapor tight cavity or pocket 258 therebetween.

It is contemplated that second layer 254 of lid 250 may be more aggressively adhered to first layer 252 of lid 250 as compared to the adhesion of first layer 252 of lid 250 to finger flange 224 of blood collector barrel 220. In this manner, as tab 254a of second layer 254 is pulled, second layer 254 is separated from first layer 252 before first layer 252 is separated from blood collector barrel 220.

Lid 250 is provided with a pad, wipe, swab or the like 260 disposed within cavity 258 and optionally adhered, bonded or otherwise secured to a surface of either first layer 252 or second layer 254. Pad 260 may be secured to lid 250 such that pad 260 is disposed or retained within cavity 258 or may be loosely disposed within cavity 258. By locating pad 260 within cavity 258, the likelihood of pad 260 drying out is reduced. Also, if desired, by locating pad 260 within cavity 258, lid 250 may be separated or peeled away from blood collector barrel 220 without exposing pad 260 to the atmosphere and the possibility of drying out.

Similar to pad 160, pad 260 is saturated with a quantity of a disinfecting solution or the like, such as, for example, for example, alcohol, benzalkonium chloride, or a solution of 70% isopropyl alcohol.

It is contemplated that pad 260 may be secured to the surface of second layer 254 of lid 250. It is further contemplated that an additional pad 261 may be secured to a back surface of first layer 252 of lid 250 and thus be disposed within cylindrical chamber 222 of blood collector barrel 220.

When using medical needle device 200, in order to disinfect the skin of the patient, the user "U" pulls on tab 254a of second layer 254 of lid 250 to separate second layer 254 from first layer 252 and expose pad 260. If desired, the skin site to be treated may be wiped with pad 260, while first layer 252 of lid 250 is still adhered to blood collector barrel 220 of medical needle device 200 such that medical needle device 200 can act as a handle for user "U." As used, herein, the term "wipe" is defined as any method of contacting a pad with the surface to be disinfected, and includes but is not limited to dabbing. It is contemplated that in order for a pad 260, impregnated or saturated with a disinfecting solution, to adhere to underlying first layer 252, that a backing layer (not shown) may be first adhered to pad 260 and the backing layer may be adhered to first layer 252. It is further contemplated that the adhesive used to secure pad 260 to backing layer would not dissolve or degrade in the presence of the disinfecting solution.

Alternatively, user "U" can detach lid 250 from blood collector barrel 220 by pulling on tab 254a of second layer 254 and thus peeling lid 250 away from blood collector barrel 220. The user "U" may then wipe or otherwise treat the skin of the patient, in the area which is to be penetrated (e.g., the needle insertion site), with pad 260 to disinfect said area.

Figure 6:
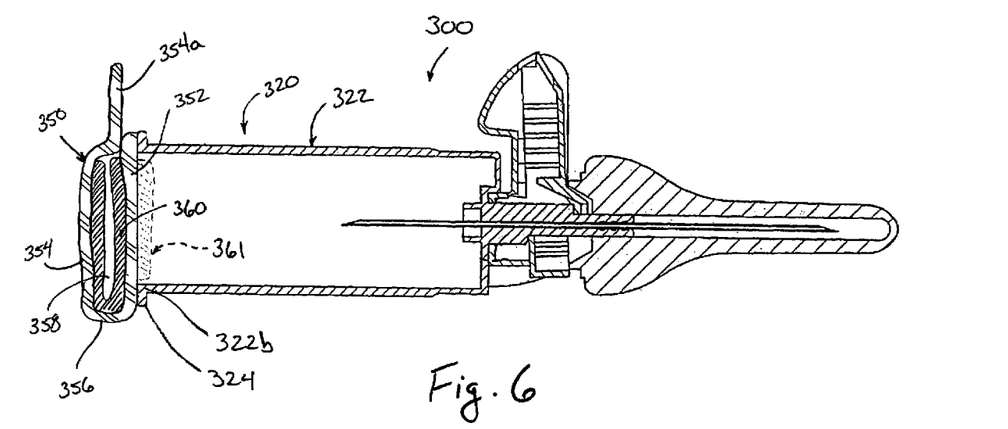
FIG. 6 is a longitudinal, cross-sectional view of a medical needle device according to yet another embodiment of the present disclosure.
Figure 7:
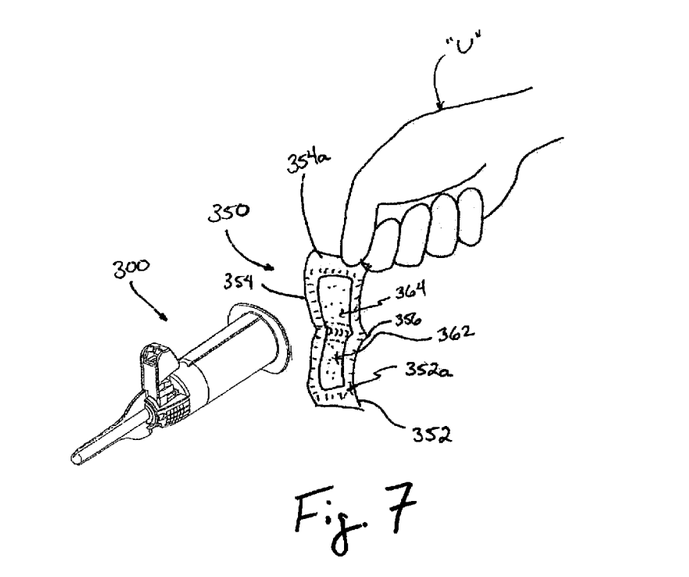
FIG. 7 is a schematic, perspective view of the medical needle device of FIG. 6, illustrating a method of use thereof.

Turning now to FIGS. 6 and 7, a medical needle device, in accordance with another embodiment of the present disclosure, is shown and generally designated as 300. Medical needle device 300 is substantially similar to medical needle devices 100, 200 and thus will only be discussed in detail to the extent necessary to identify differences in construction and operation thereof.

As shown in FIGS. 6 and 7, medical needle device 300 includes a peelable lid or the like 350 releasably secured to a finger flange 324 of blood collector barrel 320 in a fluid/vapor tight manner. Peelable lid 350 includes a first layer 352 sized to overlie open proximal end 322b of cylindrical chamber 322, and a second layer 354 connected to first layer 352 along a fold line 356. Second layer 354 is comparable in size to first layer 352 and defines a tab 354a extending therefrom for gripping by a user "U" in order to separate second layer 354 from first layer 352 and detach lid 350 from blood collector barrel 320. Second layer 354 overlies first layer 352 and may be releasably adhered to one another along a perimeter 352a of first layer 352 in order to define a fluid/vapor tight cavity or pocket 358 therebetween.

It is contemplated that second layer 354 of lid 350 may be more aggressively adhered to first layer 352 of lid 350 as compared to the adhesion of first layer 352 of lid 350 to finger flange 324 of blood collector barrel 320. In this manner, as tab 354a of second layer 354 is pulled, second layer 354 is separated from first layer 352 before first layer 352 is separated from blood collector barrel 320.

Lid 350 is provided with at least one pad, wipe, swab or the like 360 disposed within cavity 358 and optionally adhered, bonded or otherwise secured to the juxtaposed surfaces of first layer 352 and second layer 354. Pad 360 includes a first portion 362 secured to first layer 352 of lid 350, and a second portion 364 secured to second layer 354 of lid 350. First and second portions 362, 364 of pad 360 may be joined to or integrally formed with one another along fold line 356 of lid 350 or may be separate discrete pads 362, 364. Pad 360 may be secured to lid 350 such that pad 360 is disposed or retained within cavity 358 or pad 360 may be loosely disposed with cavity 358. By locating pad 360 within cavity 358, the likelihood of pad 360 drying out is reduced. Also, by locating pad 360 within cavity 358, lid 350 may be separated or peeled away from blood collector barrel 320 without exposing pad 360 to the atmosphere and the possibility of drying out. Similar to pads 160 and 260, pad 360 is saturated with a quantity of a disinfecting solution or the like, such as, for example, alcohol, benzalkonium chloride, or a solution of 70% isopropyl alcohol.

It is contemplated that an additional pad 361 may be secured to a back surface of first layer 352 of lid 350 and thus be disposed within cylindrical chamber 322 of blood collector barrel 320.

When using medical needle device 300, in order to disinfect the skin of the patient, the user "U" pulls on tab 354a of second layer 354 of lid 350 to separate second layer 354 from first layer 352 and expose pad 360. If desired, the skin site to be treated may be wiped with pad 360, while first layer 352 of lid 350 is still adhered to blood collector barrel 320 of medical needle device 300 such that medical needle device 300 can act as a handle for user "U." Similar to pad 260, pad 360 may include a backing layer (not shown) to aid in the adhesion of pad 360 to first layer 352 and/or second layer 354. Alternatively, user "U" can detach lid 350 from blood collector barrel 320 by pulling on tab 354a of second layer 354 and thus peeling first and second layers 352, 354 of lid 350 away from blood collector barrel 320. The user "U" may then wipe or otherwise treat the skin of the patient, in the area which is to be penetrated (e.g., the needle insertion site), with pad 360 to disinfect said area.

Figure 8:
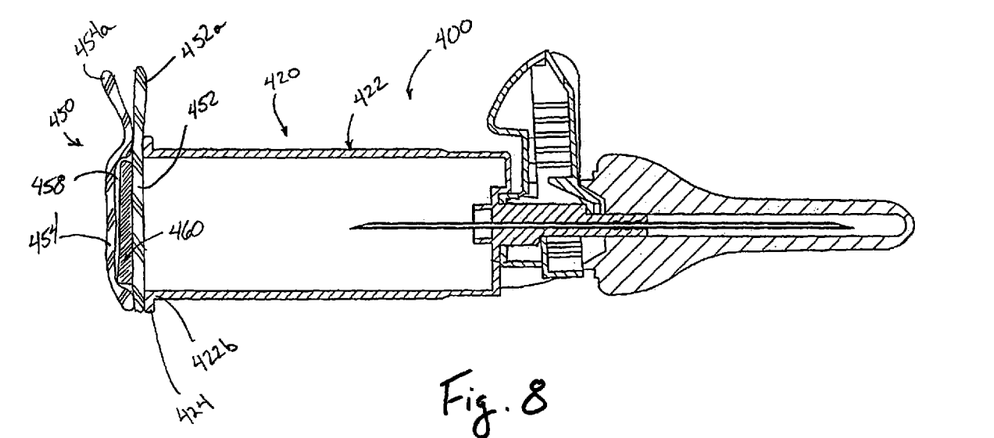
FIG. 8 is a longitudinal, cross-sectional view of a medical needle device according to still another embodiment of the present disclosure.
Figure 9A:
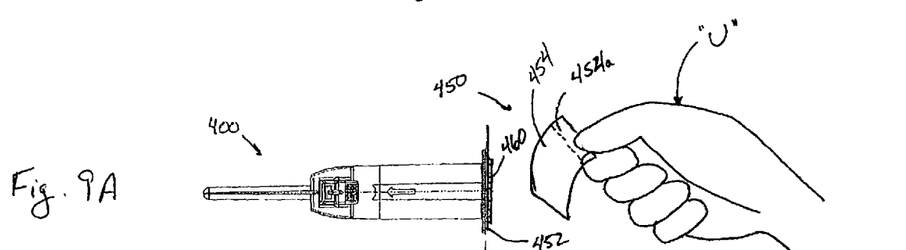
FIGS. 9A-9C are schematic views of the medical needle device of FIG. 8, illustrating a method of use thereof.
Figures 9B, 9C:
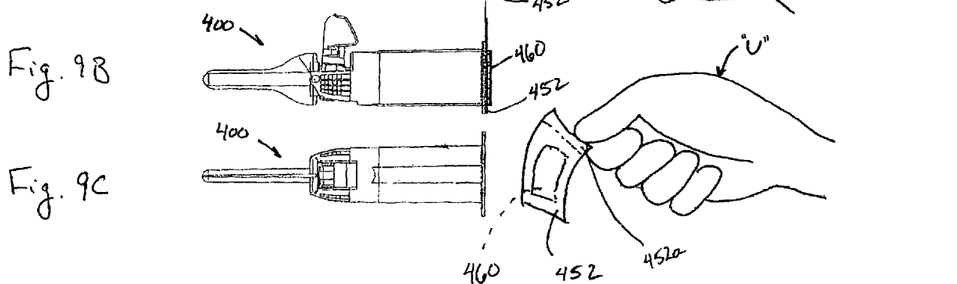

Turning now to FIGS. 8-9C, a medical needle device, in accordance with another embodiment of the present disclosure, is shown and generally designated as 400. Medical needle device 400 is substantially similar to medical needle devices 100, 200 and 300 and thus will only be discussed in detail to the extent necessary to identify differences in construction and operation thereof.

As shown in FIGS. 8-9C, medical needle device 400 includes a peelable lid or the like 450 releasably secured to a finger flange 424 of blood collector barrel 420 in a fluid/vapor tight manner. Peelable lid 450 includes a first layer 452 sized to overlie open proximal end 422b of cylindrical chamber 422, and a second layer 454 removably adhered to first layer 452 along a perimeter thereof. Second layer 454 is comparable in size to first layer 452. Each of first layer 452 and second layer 454 defines a respective tab 452a, 454a extending therefrom for gripping by a user "U" in order to separate second layer 454 from first layer 452, separate first layer 452a from blood collector barrel 420, or separate lid 450 (including first layer 452 and second layer 454) simultaneously from blood collector barrel 420. Second layer 454 overlies first layer 452 and may be releasably adhered to one another along a perimeter in order to define a fluid tight cavity or pocket 458 therebetween.

It is contemplated that second layer 454 of lid 450 may be more aggressively adhered to first layer 452 of lid 450 as compared to the adhesion of first layer 452 of lid 450 to finger flange 424 of blood collector barrel 420. In this manner, as tab 454a of second layer 454 is pulled, second layer 454 is separated from first layer 452 before first layer 452 is separated from blood collector barrel 420.

Lid 450 is provided with a pad, wipe, swab or the like 460 disposed within cavity 458 and optionally adhered, bonded or otherwise secured to a surface of either first layer 452 or second layer 454 (shown adhered to first layer 452 in FIGS. 8-9C). By locating pad 460 within cavity 458, the likelihood of pad 460 drying out is reduced. Also, by locating pad 460 within cavity 458, second layer 454 of lid 450 may be separated or peeled away from first layer 452. Similar to pads 160, 260 and 360, pad 460 may be impregnated or saturated with a quantity of a disinfecting solution or the like, such as, for example, alcohol, benzalkonium chloride, or a solution of 70% isopropyl alcohol.

When using medical needle device 400, as seen in FIGS. 9A-9C, in order to disinfect the skin of the patient, the user "U" pulls on tab 454a of second layer 454 of lid 450 to separate second layer 454 from first layer 452 and expose pad 460. If desired, the skin site to be treated may be wiped with pad 460, while first layer 452 of lid 450 is still adhered to blood collector barrel 420 of medical needle device 400 such that medical needle device 400 can act as a handle for user "U."

Similar to pads 260 and 360, pad 460 may include a backing layer (not shown) to aid in the adhesion of pad 460 to first layer 452. It is contemplated that the adhesion strength of pad 460 to first layer 452 is greater than the adhesion strength of first layer 452 to blood collector barrel 420.

Figure 10:
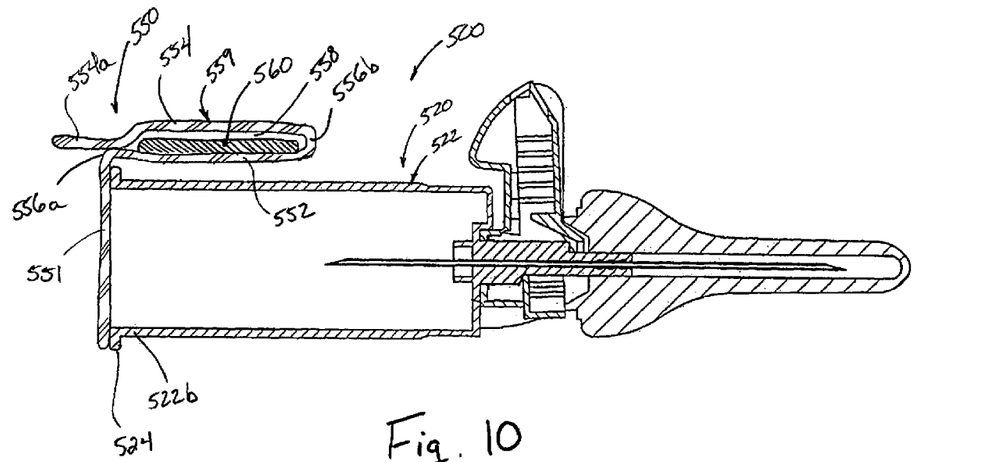
FIG. 10 is a longitudinal, cross-sectional view of a medical needle device according to another embodiment of the present disclosure.
Figure 11:
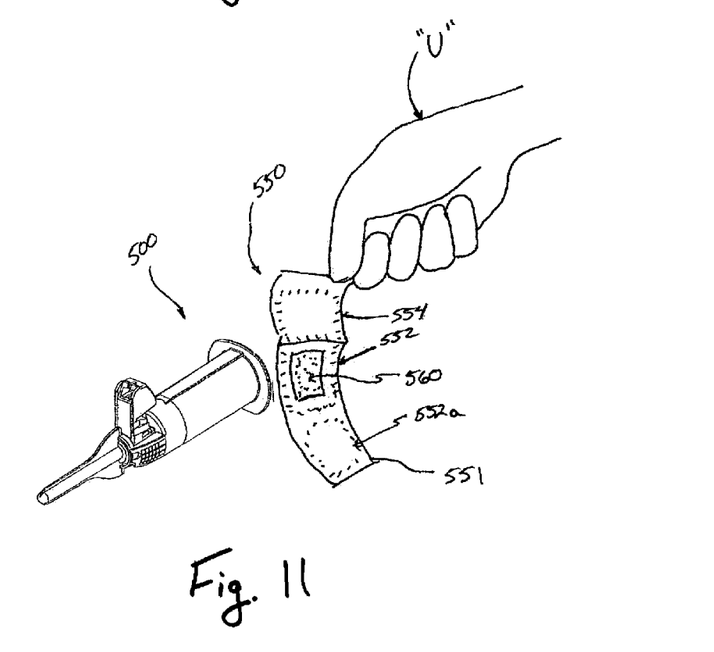
FIG. 11 is a schematic, perspective view of the medical needle device of FIG. 10, illustrating a method of use thereof.

Turning now to FIGS. 10 and 11, a medical needle device, in accordance with another embodiment of the present disclosure, is shown and generally designated as 500. Medical needle device 500 is substantially similar to medical needle devices 100, 200, 300 and 400 and thus will only be discussed in detail to the extent necessary to identify differences in construction and operation thereof.

As shown in FIGS. 10 and 11, medical needle device 500 includes a peelable lid or the like 550 releasably secured to a finger flange 524 of blood collector barrel 520 in a fluid/vapor tight manner. Peelable lid 550 includes a flap 551 sized to overlie open proximal end 522b of cylindrical chamber 522 and be secured to finger flange 524 of blood collector barrel 520, a first layer 552 extending from flap 551 along a fold line 556a, and a second layer 554 connected to first layer 552 along a fold line 556b and removably adhered to first layer 552 along a perimeter 552a of first layer 552. Second layer 554 is comparable in size to first layer 552. Second layer 554 overlies first layer 552 and may be releasably adhered to one another along a perimeter in order to define a fluid/vapor tight cavity or pocket 558 therebetween and define a pouch 559. Second layer 554 defines a tab 554a extending therefrom for gripping by a user "U" in order to separate second layer 554 from first layer 552 and/or to separate lid 550 (including flap 551, first layer 552 and second layer 554) from blood collector barrel 520.

Fold line 556a may be provided with a line of reduced thickness or weakness, or a series of perforations or the like in order to enable a user "U" to detach or separate pouch 559 from flap 551. Fold line 556a of lid 550 enables a user "U" to lay pouch 559 against blood collector barrel 520 (see FIG. 10) or against flap 551 (not shown).

Lid 550 is provided with a pad, wipe, swab or the like 560 disposed within cavity 558 and optionally adhered, bonded or otherwise secured to a surface of either first layer 552 or second layer 554 (shown adhered to first layer 552 in FIGS.

10 and 11). By locating pad 560 within cavity 558, the likelihood of pad 560 drying out is reduced. Also, by locating pad 560 within cavity 558, second layer 554 of lid 550 may be separated or peeled away from first layer 552. Similar to pads 160, 260, 360 and 460, pad 560 is saturated with a quantity of a disinfecting solution or the like, such as, for example, alcohol, benzalkonium chloride, or a solution of 70% isopropyl alcohol.

Similar to pad 360, it is contemplated that pad 560 may include a first portion secured to first layer 552 of lid 550, and a second portion secured to second layer 554 of lid 550. The first and second portions of pad 560 may be joined to or integrally formed with one another along a fold line of lid 550 or may be separate discrete pads.

When using medical needle device 500, in order to disinfect the skin of the patient, the user "U" pulls on tab 554a of second layer 554 of lid 550 to separate second layer 554 from first layer 552 and expose pad 560. Alternatively, the user "U" may detach pouch 559 from flap 551, along fold line 556a, and then open pouch 559 by separating second layer 554 from first layer 552.

Figure 12:
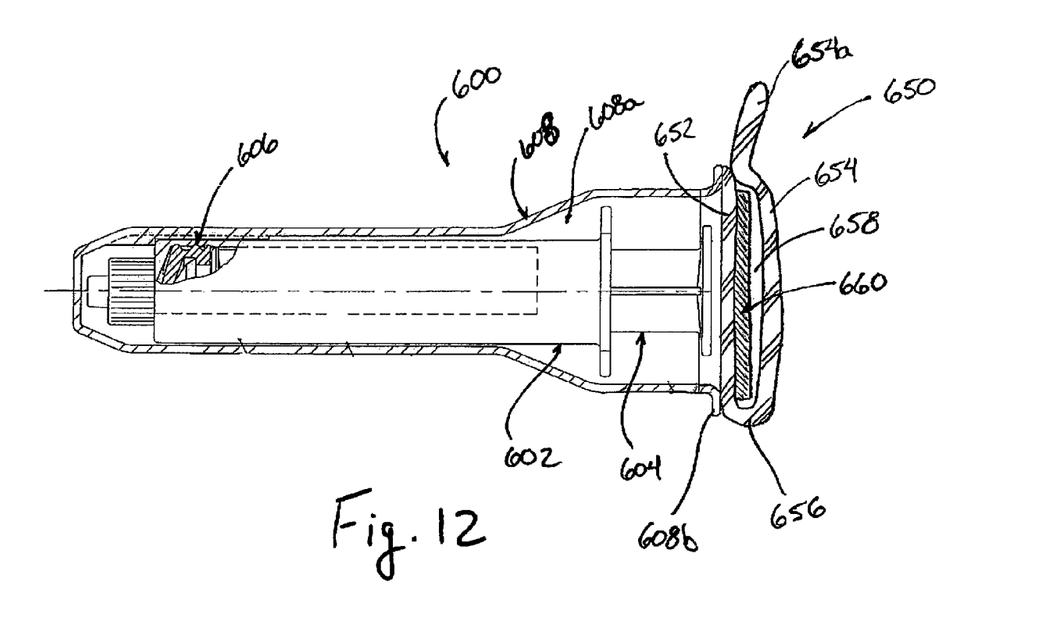
FIG. 12 is a longitudinal, cross-sectional view a syringe-type medical needle device, stored in a hard-pack, in accordance with the principles of the present disclosure.

Turning now to FIG. 12, a medical assembly, in the form of a syringe assembly, is shown and generally designated as 600. Syringe assembly 600 includes a syringe barrel 602 and a plunger 604 slidably disposed within barrel 602. Plunger 604 includes a plunger tip 606 connected to a distal end of plunger 604 and which is in fluid/vapor tight contact with an inner surface of barrel 602. Syringe assembly 600 includes a container or sleeve 608 configured and dimensioned to retain syringe barrel 602 and plunger 604 within an open ended cavity 608a thereof. Sleeve 608 is configured to retain syringe barrel 602 and plunger 604 within cavity 608a when plunger 606 is in a substantially fully advanced position relative to syringe barrel 602.

As shown in FIG. 12, syringe assembly 600 includes a peelable lid or the like 650 releasably secured to a finger flange 608b of sleeve 608 in a fluid/vapor tight manner. Peelable lid 650 includes a first layer 652 sized to overlie the open end of cavity 608a of sleeve 608, and a second layer 654 connected to first layer 652 along a fold line 656. Second layer 654 is comparable in size to first layer 652 and defines a tab 654a extending therefrom for gripping by a user "U" in order to separate second layer 654 from first layer 652 and detach lid 650 from blood collector barrel 620. Second layer 654 overlies first layer 652 and may be releasably adhered to one another along a perimeter thereof in order to define a fluid/vapor tight cavity or pocket 658 therebetween.

It is contemplated that second layer 654 of lid 650 may be more aggressively adhered to first layer 652 of lid 650 as compared to the adhesion of first layer 652 of lid 650 to sleeve 608. In this manner, as tab 654a of second layer 654 is pulled, second layer 654 is separated from first layer 652 before first layer 652 is separated from sleeve 608.

Lid 650 is provided with a pad, wipe, swab or the like 660 disposed within cavity 658 and optionally adhered, bonded or otherwise secured to a surface of either first layer 652 and/or second layer 654. Pad 660 may be secured to lid 650 such that pad 660 is disposed or retained within cavity 658 or pad 660 may be loosely disposed within cavity 658. By locating pad 660 within cavity 658, the likelihood of pad 660 drying out is reduced. Also, by locating pad 660 within cavity 658, lid 650 may be separated or peeled away from sleeve 608 without exposing pad 660 to the atmosphere and the possibility of drying out. Similar to pads 160-560, pad 660 is saturated with a quantity of a disinfecting solution or the like, such as, for example, alcohol, benzalkonium chloride, or a solution of 70% isopropyl alcohol.

It is contemplated that pad 660 may be secured to the surface of second layer 654 of lid 650. It is further contemplated that an additional pad may be secured to a back surface of first layer 652 of lid 650 (not shown) and thus be disposed within cavity 608a of sleeve 608.

Similar to pad 360, it is contemplated that pad 660 may include a first portion secured to first layer 652 of lid 650, and a second portion secured to second layer 654 of lid 650. The first and second portions of pad 660 may be joined to or integrally formed with one another along a fold line of lid 650 or may be separate discrete pads.

When using syringe assembly 600, in order to disinfect the skin of the patient, the user "U" pulls on tab 654a of second layer 654 of lid 650 to separate second layer 654 from first layer 652 and expose pad 660. If desired, the skin site to be treated may be wiped with pad 660, while first layer 652 of lid 650 is still adhered to sleeve 608 of syringe assembly 600 such that sleeve 608 can act as a handle for user "U." Alternatively, user "U" can detach lid 650 from sleeve 608 by pulling on tab 654a of second layer 654 and thus peeling lid 650 away from sleeve 608. The user "U" may then wipe or otherwise treat the skin of the patient, in the area which is to be penetrated (e.g., the needle insertion site), with pad 660 to disinfect said area.

While syringe assembly 600 has been shown and described with lid 650, it is contemplated and within the scope of the present disclosure for syringe assembly 600 to be provided with a lid 150, 350, 450 or 550 are described above in relation to medical needle devices 100, 300, 400 or 500, respectively.

Figure 13:
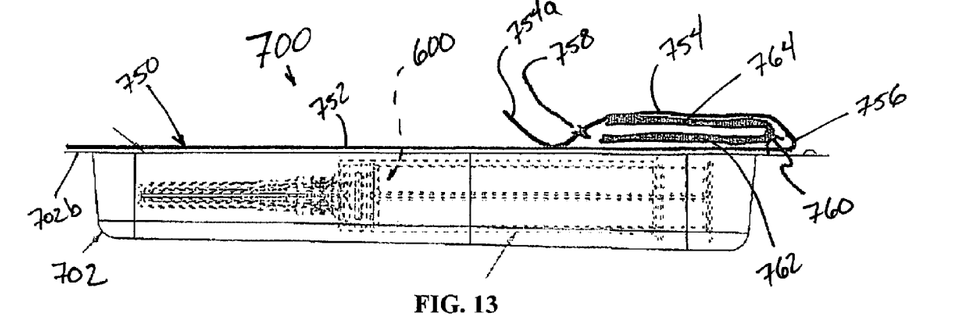
FIG. 13 is a side, elevational view of a syringe-type medical needle device, stored in a storage container, in accordance with the principles of the present disclosure.
Figure 14:
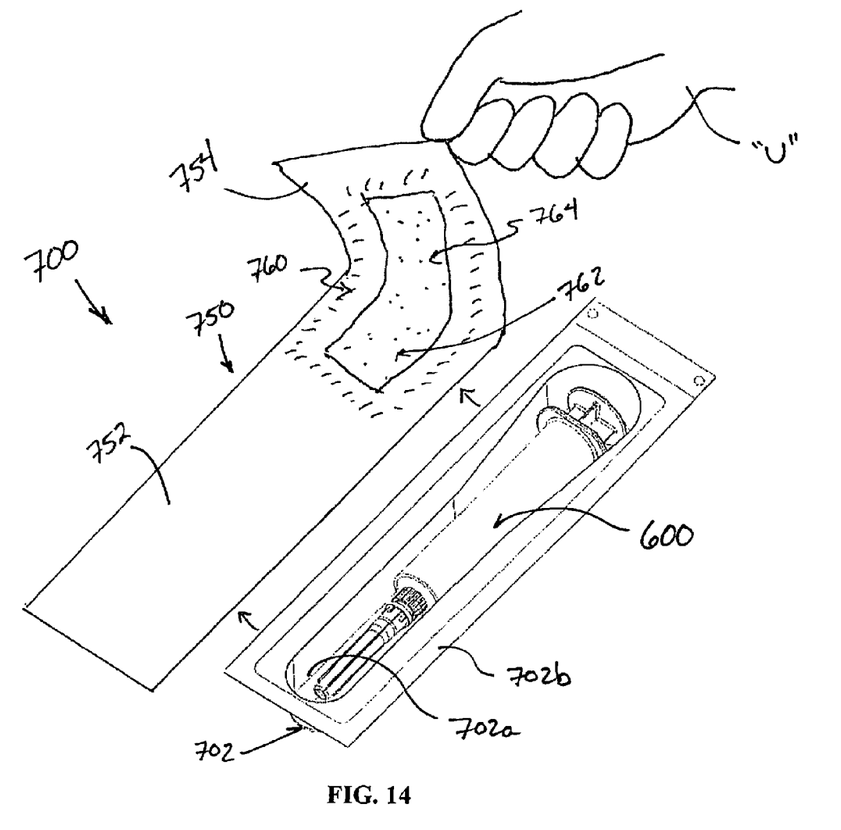
FIG. 14 is a perspective view of the storage container of FIG. 13, illustrating a method of use thereof.

Turning now to FIGS. 13 and 14, a medical storage container, in the form of a medical syringe tray, blister pack or hard-pack, is shown and generally designated as 700. Medical storage container 700 is configured and dimensioned to releasably retain/store a medical device (i.e., a medical needle syringe assembly 600 or the like) therein.

Medical storage container 700 includes a main body portion 702 defining a cavity 702a configured and dimensioned to receive and store medical needle syringe assembly 600. Medical storage container 700 may include a flange 702b extending around at least a portion of an upper edge of main body portion 702.

Medical storage container 700 may be fabricated from a fluid/vapor impermeable material and at least a portion of which may be fabricated from a translucent or transparent material.

As shown in FIGS. 13 and 14, medical storage container 700 includes a peelable lid or the like 750 releasably secured to flange 702b of body portion 702 in a fluid/vapor tight manner. Peelable lid 750 includes a first layer 752 sized to overlie the open end of cavity 702a of body portion 702, and a second layer 754 connected to first layer 752 along a fold line 756. Second layer 754 is relatively smaller in size as compared to first layer 752 and defines a tab 754a extending therefrom for gripping by a user "U" in order to separate second layer 754 from first layer 752 and to detach lid 750 from medical storage container 700. Second layer 754 overlies at least a portion of first layer 752 and may be releasably adhered to one another along a perimeter of second layer 754 in order to define a fluid/vapor tight cavity or pocket 758 therebetween.

It is contemplated that second layer 754 of lid 750 may be more aggressively adhered to first layer 752 of lid 750 as compared to the adhesion of first layer 752 of lid 750 to body portion 702. In this manner, as tab 754a of second layer 754 is pulled, second layer 754 is separated from first layer 752 before first layer 752 is separated from body portion 702.

Lid 750 is provided with a pad, wipe, swab or the like 760 disposed within cavity 758 and optionally adhered, bonded or otherwise secured to a surface of either first layer 752 and/or second layer 754. Pad 760 includes a first portion 762 secured to first layer 752 of lid 750, and a second portion 764 secured to second layer 754 of lid 750. First and second portions 762, 764 of pad 760 may be joined to or integrally formed with one another along fold line 756 of lid 750 or may be separate discrete pads 762, 764. Pad 760 may be secured to lid 750 such that pad 760 is disposed or retained within cavity 758 or pad 760 may be loosely disposed with cavity 758. By locating pad 760 within cavity 758, the likelihood of pad 760 drying out is reduced. Also, by locating pad 760 within cavity 758, lid 750 may be separated or peeled away from body portion 702 without exposing pad 760 to the atmosphere and the possibility of drying out.

In an embodiment, it is contemplated that lid 750 is not provided with a second layer 754 and that pad 760 is secured to an inner surface of first layer 752 such that pad 760 is contained within a fluid/vapor tight environment. In this manner, lid 750 would function in substantially the same manner as lid 150.

Pad 760 may be saturated with a quantity of a disinfecting solution or the like, such as, for example, alcohol, benzalkonium chloride, or a solution of 70% isopropyl alcohol.

When a user "U" intends to use syringe assembly 600 contained in medical storage container 700, prior to using syringe assembly 600, in order to disinfect the skin of the patient, the user "U" pulls on tab 754a of second layer 754 of lid 750 to separate second layer 754 from first layer 752 and expose pad 760. The skin site to be treated may then be wiped with pad 760 to disinfect said site.

Any of the aforementioned lids 150-750 may be fabricated in whole or in part from an elastomeric, fluid/vapor impervious material such as, for example, sheets of polyvinylchloride (PVC), polyethylene and the like lined or coated with a layer of aluminum or the like.

Pads 160-760 may be fabricated from cotton, gauze, nonwoven fabric or the like.

Reference may be made to U.S. patent application Ser. No. 11/716,502, filed on Mar. 8, 2007, entitled "Safety Shield Apparatus and Mounting Structure for Use with Medical Needle Devices," published as US2007/0282275; and International Patent Application Serial No. PCT/US2007/010194, filed on Apr. 26, 2007, entitled "Safety Shield Apparatus and Mounting Structure for Use with Medical Needles," published as WO2007/127345 the entire content of each of which is incorporated herein by reference, for a detailed discussion of the construction and/or operation of blood collection devices 100, 200, 300, 400 and 500.

It will be understood that various modifications may be made to the embodiments disclosed herein. Although the above description is described in association with a blood collection device and/or a syringe assembly, it is envisioned that the presently disclosed lids and the like may be used with other medical needle devices. Therefore, the above description should not be construed as limiting, but merely as exemplifications of preferred embodiments. Those skilled in the art will envision other modifications within the scope and spirit of the claims appended hereto.

What is claimed is:

1. A medical needle device comprising:
 a barrel having an open first end and a second end having an opening configured to support a needle, the barrel defining a cavity in fluid communication with the opening, the cavity being configured to receive a blood collection tube;
 a lid releasably connected to and overlying the open first end of the barrel, an axial surface of the lid facing the cavity of the barrel; and
 a pad secured to the axial surface of the lid and disposed within the cavity of the barrel when the lid is connected to the barrel, the lid being positioned such that the pad extends into and is exposed to the cavity of the barrel when the lid is connected to the barrel, wherein the pad comprises a disinfecting solution.

2. The medical needle device according to claim 1, wherein the disinfecting solution is one of alcohol, isopropyl alcohol and benzalkonium chloride.

3. The medical needle device according to claim 1, wherein the lid is adhered to the barrel in at least one of a fluid tight and vapor tight manner.

4. The medical needle device according to claim 2, wherein the lid includes a tab extending therefrom.

5. The medical needle device according to claim 2, wherein the lid is fabricated from at least one of a fluid impermeable material and a vapor impermeable material.

6. The medical needle device according to claim 1, wherein the medical needle device is a blood collection device.

7. The medical needle device according to claim 1, wherein the medical needle device is a syringe.

8. A medical needle device including a barrel having an open first end and capable of supporting a needle at a second end of the barrel, the medical needle device comprising:
 a lid releasably connected to the barrel, the lid including:
  a first layer releasably adhered to and overlying the open first end of the barrel; and
  a second layer releasably adhered to the first layer, wherein the first layer and the second layer define at least one of a fluid and vapor tight pocket therebetween, wherein the second layer of the lid is adhered to the first layer of the lid such that upon application of force, the second layer is separated from the first layer before the lid is separated from the barrel; and
 a pad disposed within the pocket of the lid, wherein the pad comprises a disinfecting solution.

9. The medical needle device according to claim 8, wherein the disinfecting solution is one of alcohol, isopropyl alcohol and benzalkonium chloride.

10. The medical needle device according to claim 8, wherein the lid includes a tab extending from and integrally connected with the second layer.

11. The medical needle device according to claim 8, wherein the second layer is integrally connected to the first layer along a fold line.

12. The medical needle device according to claim 8, wherein the lid includes an additional pad secured to the first layer at a location within the barrel.

13. The medical needle device according to claim 8, wherein the pad is secured to one of the first layer and the second layer within the pocket.

14. The medical needle device according to claim 8, wherein the second layer is integrally connected to the first layer along a fold line, and wherein the pad is secured to and extends between the first layer and the second layer.

15. The medical needle device according to claim 14, wherein the lid includes a tab extending from and integrally connected with the second layer.

16. The medical needle device according to claim 14, wherein the first layer and the second layer of the lid are fabricated from at least one of a fluid impermeable material and a vapor impermeable material.

17. The medical needle device according to claim 12, wherein the first layer of the lid includes a flap extending therefrom and integrally connected therewith, wherein the flap of the first layer is releasably adhered to and overlies the open first end of the barrel, and wherein the flap is dimensioned such that the pocket of the lid is positionable against an outer surface of the medical needle device.

18. The medical needle device according to claim 17, wherein the lid includes a tab extending from and integrally connected with the second layer.

19. The medical needle device according to claim 17, wherein the first layer and the second layer of the lid are fabricated from at least one of a fluid impermeable material and a vapor impermeable material.

20. A medical device comprising:
    a barrel having an open first end and a second end having an opening configured to support a needle, the barrel defining a cavity in fluid communication with the opening, the cavity being configured to receive a blood collection tube;
    a lid releasably adhered to and overlying the open first end of the barrel in at least one of a fluid tight manner and a vapor tight manner, an axial surface of the lid facing the cavity of the barrel; and
    a pad secured to the axial surface of the lid such that the pad is disposed within the cavity of the barrel when the lid is adhered to the barrel, the lid being positioned such that the pad extends into and is exposed to the cavity of the barrel when the lid is connected to the barrel, wherein the pad is saturated with a disinfecting solution.

21. The medical device according to claim 20, wherein the disinfecting solution is one of alcohol, isopropyl alcohol and benzalkonium chloride.

22. The medical device according to claim 20, wherein the lid includes a tab extending therefrom.

23. The medical device according to claim 20, wherein the lid is fabricated from at least one of a fluid impermeable material and a vapor impermeable material.

24. A method of collecting a fluid sample from a patient, the method comprising the steps of:
    providing a medical needle device including a barrel having an open first end and supporting a needle at a second end of the barrel, the barrel defining a cavity in fluid communication with the needle, the cavity being configured to receive a blood collection tube, the medical needle device including:
        a lid releasably connected to and overlying the open first end of the barrel, an axial surface of the lid facing the cavity of the barrel; and
        a pad secured to the axial surface of the lid and disposed within the cavity of the barrel when the lid is connected to the barrel, the lid being positioned such that the pad extends into and is exposed to the cavity of the barrel when the lid is connected to the barrel, the pad comprising a disinfecting solution;
    peeling the lid away from the medical needle device to expose the pad;
    wiping the pad across an area of the skin of the patient to be penetrated by the needle of the medical needle device; and
    penetrating the skin of the patient, in the area wiped by the pad, with the needle of the medical needle device.

25. A method of collecting a fluid sample from a patient, the method comprising the steps of:
    providing a medical needle device including a barrel having an open first end and supporting a needle at a second end of the barrel, the medical needle device including:
        a lid releasably connected to the barrel, the lid including:
            a first layer releasably adhered to and overlying the open first end of the barrel; and
            a second layer releasably adhered to the first layer, wherein the first layer and the second layer define at least one of a fluid and vapor tight pocket therebetween, wherein the second layer of the lid is adhered to the first layer of the lid such that upon application of force, the second layer is separated from the first layer before the lid is separated from the barrel; and
        a pad disposed within the pocket of the lid, wherein the pad comprises a disinfecting solution;
    peeling the first layer of the lid at least partially away from the second layer of the lid to expose the pad;
    removing the pad from the pocket;
    wiping the pad across an area of the skin of the patient to be penetrated by the needle of the medical needle device; and
    penetrating the skin of the patient, in the area wiped by the pad, with the needle of the medical needle device.

\* \* \* \* \*